(12) United States Patent
You et al.

(10) Patent No.: US 6,770,457 B1
(45) Date of Patent: Aug. 3, 2004

(54) PROCESS OF PURIFYING ANGIOGENESIS INHIBITORS

(75) Inventors: Weon Kyoo You, Kyonggi-do (KR); Seung Ho So, Taejon-si (KR); Byung Cheul Ahn, Kyonggi-do (KR); Hyosil Lee, Kyonggi-do (KR); Soo-Il Jung, Kyonggi-do (KR); Young jo Kim, Kyonggi-do (KR); Jong Hyuk Lee, Seoul (KR); Yong-Kil Hong, Seoul (KR); Young Ae Joe, Seoul (KR); Soo-Ik Chang, Chungcheongbuk-do (KR)

(73) Assignee: Korea Green Cross Corporation, Kyonggi-do (KR)

( * ) Notice: Subject to any disclaimer, the term of this patent is extended or adjusted under 35 U.S.C. 154(b) by 0 days.

(21) Appl. No.: 09/701,265

(22) PCT Filed: May 28, 1999

(86) PCT No.: PCT/KR99/00263

§ 371 (c)(1),
(2), (4) Date: Nov. 27, 2000

(87) PCT Pub. No.: WO99/61464

PCT Pub. Date: Dec. 2, 1999

(30) Foreign Application Priority Data

May 28, 1998 (KR) .............................. 98-19535
May 27, 1999 (KR) ........................... 1999-19144

(51) Int. Cl.⁷ .............................................. C12P 21/06
(52) U.S. Cl. ............... 435/69.1; 435/320.1; 435/252.8; 530/350; 530/412
(58) Field of Search ................ 435/69.1, 320.1, 435/252.8; 530/412, 416, 350

(56) References Cited

U.S. PATENT DOCUMENTS 5,854,048 A * 12/1998 Martin et al. ................ 435/212
5,908,625 A * 6/1999 Kohnert et al. ............. 424/94.1
5,973,118 A * 10/1999 Kohnert et al. ............. 530/350
6,024,688 A * 2/2000 Folkman et al. .............. 514/12

FOREIGN PATENT DOCUMENTS

WO  WO 96/35774  11/1996
WO  WO 97/41824  11/1997
WO  WO 99/16889  4/1999

OTHER PUBLICATIONS

Vandenbroeck K, et al. Eur J Biochem Jul. 15, 1993; 215 (2): 481–6.*
Stoyan T, et al. Eur J Biochem Aug. 15, 1993; 216 (1): 239–45.*
Guise AD, et al. Mol Biotechnol Aug. 1996; 6 (1): 53–64.*
Skolnick J, et al. Trends Biotech Jan. 2000; 18: 34–39.*
Haelewyn J, et al. Biochem Mol Biol Int Dec. 1995; 37 (6): 1163–71.*
Arora D, et al. J Biotechnol Dec. 10, 1996; 52 (2): 127–33.*
Cleary S, et al. Biochem 1989; 28 (4): 1884–91.*
Cao Y, et al. J Biol Chem Nov. 15, 1996; 271 (46): 29461–7.*
Menhart N, et al. Biochem 1993; 32: 8799–806.*
Menhart N, et al. Biochem 1991; 30: 1948–57.*
Yihai Cao et al., "Kringle 5 of Plasminogen is a Novel Inhibitor of Endothelial Cell Growth", *The Journal of Biological Chemistry*, vol. 272, No. 36, Sep. 5, 1997, pp. 22924–22928.
Yihai Cao et al., "Kringle Domains of Human Angiostatin: Characterization of the Anti–proliferative Activity of Endothelial Cells", *The Journal of Biological Chemistry*, vol. 271, No. 46, Nov. 15, 1996, 29461–29467.
Weidong–Richard Ji et al., "Characterization of Kringle Domains of Angiostatin as Antagonists of Endothelial Cell Migration, an Important Process in Angiogenesis", *The FASEB Journal*, Dec. 1998, pp. 1731–1738.

* cited by examiner

Primary Examiner—Anthony C. Caputa
Assistant Examiner—Stephen L. Rawlings
(74) Attorney, Agent, or Firm—Gates & Cooper LLP

(57) ABSTRACT

The present invention relates to process of purifying the angiogensis inhibitor proteins expressed in *E. coli* and to the use of recombinant kringle 1–3 (; greenstatin) purified by the above process as a angiogenesis inhibitor and an anticancer agent. Particularly, according to the process of purifying the protein, the angiogenesis inhibitor proteins overexpressed are solubilized, refolded, and purified as a pure and active form. The greenstatin purified by the process specifically suppresses endothelial cell proliferation, anaiogenesis, and the growth of lung cancer, skin cancer, and brain tumor. Therefore, the process of this invention is applicable to the mass-production of angiogenesis inhibitor proteins such as greenstatin which is useful for the treatment of glaucoma, retinopathy, and cancers.

8 Claims, 8 Drawing Sheets

FIG. 7A
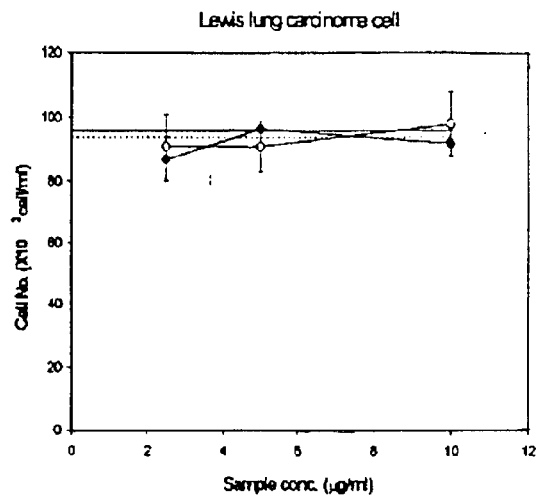
FIG. 7B
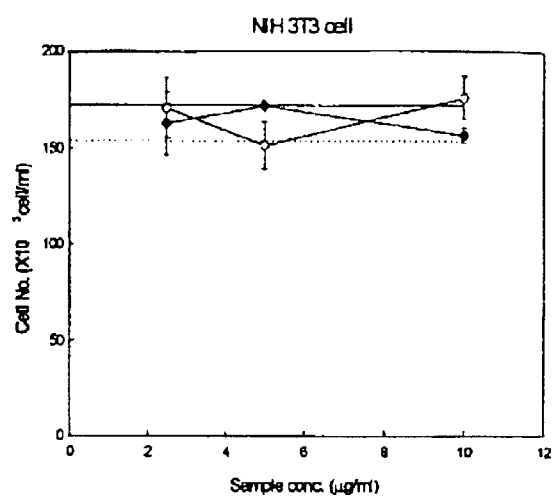
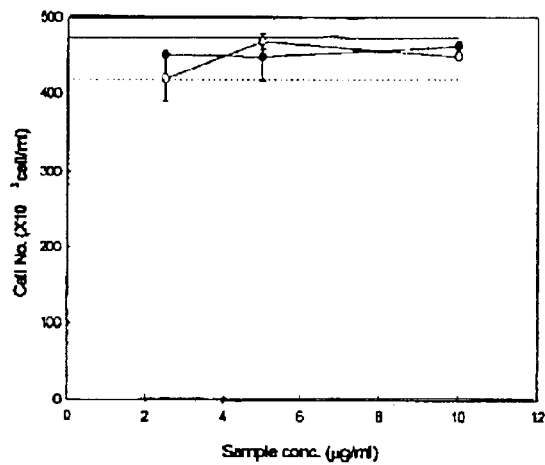
FIG. 7C

PBS rPK1-3

+ A

+ A + rPK1-3

PBS             rPK1-3

PROCESS OF PURIFYING ANGIOGENESIS INHIBITORS

FIELD OF THE INVENTION

The present invention relates to a process of purifying angiogenesis inhibitor proteins that are expressed in *E. coli*, and also relates to the use of recombinant kringle 1–3 of plasminogen (hereinafter, referred to as "greenstatin") purified according to the above process as an angiogenesis inhibitor or as an anticancer agent.

BACKGROUND

Angiogenesis is a biological process in which new blood vessel is generated from an existing vessel. Regulated by tight controlling mechanism, angiogenesis is involved in special physiological cases such as wound healing and tissue regeneration. In diseases such as arthritis, diabetic retinopathy, psoriasis, and so on, angiogenesis also happens and converts these diseases into clinical malignancies. Furthermore, angiogenesis is essential to the growth and metastasis of cancer cells. To grow more than 1–2 mm$^3$, cancer tissues should be supplied for nutrients, oxygen, and growth actors from new blood vessels induced by angiogenesis (Fidler e, al., Cell, 79 185–88, 1994). Moreover, cancer cells can be metastasized to other tissues through the new blood vessels.

Current cancer therapies mainly include operative therapy, chemotherapy, and radiotherapy. While chemotherapy has the advantage of convenient administration, its disadvantages include nonspecific attack for normal cells, poor uptake on cancer tissue, and drug tolerance. Due to these disadvantages, chemotherapy for cancer is associated with various side effects and poor efficacy, and often cannot be employed repeatedly. Although radiotherapy has been developed, it is also associated with nonspecific effects on normal cells. Thus, anticancer therapy that will cover the side effects of the existing therapies has been required, which will improve current anticancer therapies or make up for their disadvantages.

As a revolutionary anticancer agent, angiogenesis inhibitors have been studied. To treat the angiogenesis-dependent diseases such as cancers, arthritis, diabetic retinopathy, and psoriasis, various angiogenesis inhibitors have been developed last 20 years, and more than 11 inhibitors have been under preclinical or clinical phase. These inhibitors vary in their inhibition mechanisms and inhibition efficiencies.

The angiogenesis inhibitors under clinical or preclinical phase include metastasis inhibitors such as batimastar, cancer growth inhibitors such as interferon and VEGF (; Vascular Endothelial Growth Factor), and natural cryptic proteins such as angiostatin™ (first four kringle domains of plasminogen, SEQ ID NO: 2) and endostatin. Of these inhibitors, angiostatin™ and endostatin are inactive in a native form, but have an angiogenesis inhibitor activity in a cleaved form (Gradishar, *Invest. New Drugs*, 15, 49–59, 1997; Bergers et al., *Science*, 284, 808–812, 1999).

Angiostatin™ is a protein containing the kringle 1 to 4 region of plasminogen (described by SEQ ID NO: 1), a thrombolysis factor. The amino acid sequence of angiostatin™ (described by SEQ ID NO: 2) is the part (99th~467th amino acid residues) of full plasminogen sequence. On the other hand, greenstatin (described by SEQ ID NO: 3) is a recombinant protein which consists of 254 amino acid residues (101~354). Kringle 4 is deleted in greenstatin but contained in angiostatin™.

The purification of recombinant angiostatin™ is laborious since there are 13 disulfide bonds in the angiostatin™ protein structure. To overcome the difficulties in renaturation of angiostatin™ during purification step, two methods for producing angiostatin™ are currently used. In one method, angiostatin™ is isolated from the plasminogen, as a mixture of kringle 1–3 fragment and kringle 1–4 fragment. The other method exploits yeast or baculovirus system in which recombinant angiostatin™ is produced as a soluble form.

Since greenstatin also has 10 intramolecular disulfide bonds, it is hard to purify and currently expressed and purified in the yeast or baculovirus system. However, on account of the low yield and the high cost, the yeast or baculovirus system is not so efficient and economical.

Although *E. coli* expression system is preferable for the inexpensive and convenient mass-production of angiogenesis inhibitor proteins such as angiostatin™ and greenstatin, it is not suitable for the production of eukaryotic proteins in which sugar chains or the high order of protein folding is required for the activities of the recombinant proteins. Thus, in the *E. coli* system producing the angiogenesis inhibitor proteins, unfolding and refolding processes as well as the expression and purification processes should be optimized to meet with the structural requisite for proper activities.

We, the inventors of the present invention, have investigated the optimized process of purifying the angiogenesis inhibitor proteins such as angiostatin™ and greenstatin, which allows the efficient mass-production of the proteins. In this invention, we construct an *E. coli* expression vector into which DNA sequence encoding an angiogenesis inhibitor protein is inserted; transform *E. coli* with this vector; purify the inhibitor protein from the inclusion bodies of the *E. coli* transformant; perform refolding reaction in the presence of basic amino acids; and perform further purification. This invention is performed by confirming that these processes can be used to massively produce active form of angiogenesis inhibitor proteins, and that the active greenstatin purified according to the processes is applicable for the suppression of angiogenesis in vivo and of angiogenesis-dependent diseases.

SUMMARY OF THE INVENTION

It is an object of this invention to provide the optimized purifying process allowing the efficient mass-production of angiogenesis inhibitor proteins such as angiostatin and greenstatin.

In such aspect of this invention, the process of purifying angiogenesis inhibitor proteins comprises the steps of;

1) constructing an *E. coli* expression vector containing DNA sequence encoding an angiogenesis inhibitor protein, transforming *E. coli* with the vector, and producing the angiogenesis inhibitor protein in the inclusion bodies of *E. coli* transformant;
2) solubilizing the inclusion bodies of step 1);
3) refolding the solubilized fraction of step 2) in a buffer containing urea and glutathione;

It is an additional object of this invention to provide the use of greenstatin purified according to the purifying process for the treatment of cancers including lung cancer, skin cancer, and brain tumor, and of ophthalmic diseases including glaucoma and retinopathy.

Further objects and advantages of the present invention will be disclosed hereinafter.

Figure 5:
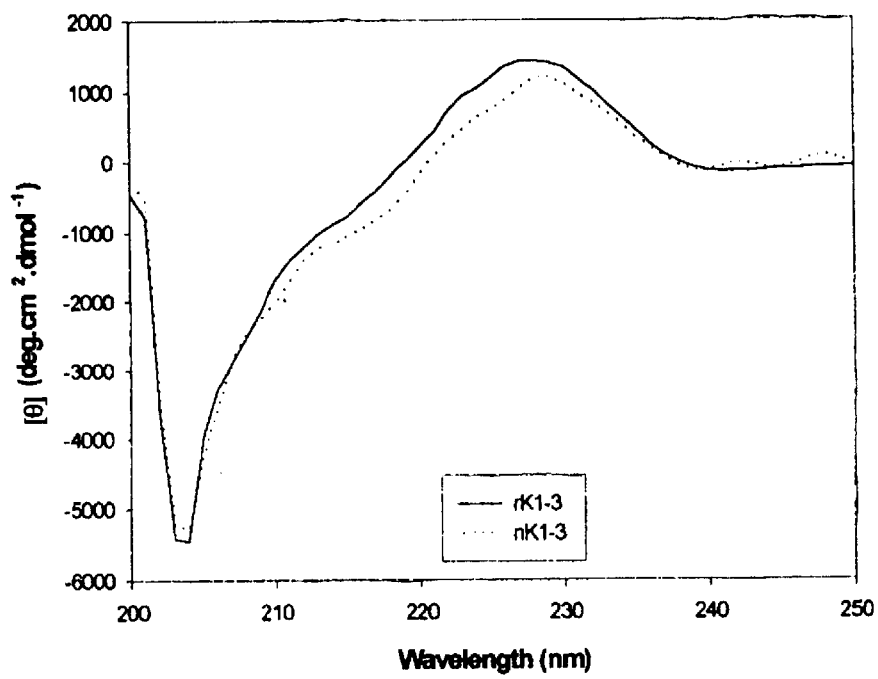
Figure 6:
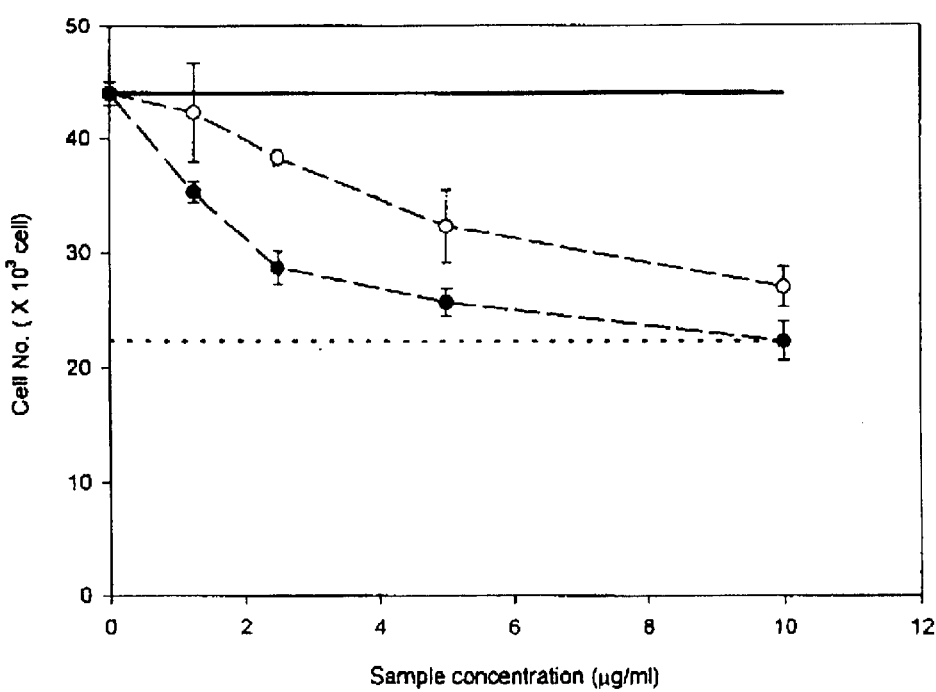

Lane 2: inclusion bodies isolates of expression-induced *E. coli*;

Lane 3: purified greenstatin;

Lane 4: purified greenstatin (non-reducing),

FIG. 5 represents the secondary structures of proteins, using circular dichroism, where solid line: chromatograph of native greenstatin;

dot line: chromatograph of recombinant greenstatin,

FIG. 6 represents the inhibitory activities of purified greenstatin and native angiostatin™ in the growth inhibition of bovine capillary endothelial cells, where closed circle: purified greenstatin-treated cells;

open circle: native angiostatin™-treated cells;

solid line: bFGF (1 ng/ml)-treated control;

dot line: PBS-treated control,

FIG. 7(A–C) represents that neither greenstatin or angiostatin™ has effect on the proliferation of non-endothelial cells, where closed circle: greenstatin-treated cells;

open circle: native angiostatin™-treated cells;

solid line: bFGF (1 ng/ml)-treated control;

dot line: PBS-treated control.

Figure 8A:
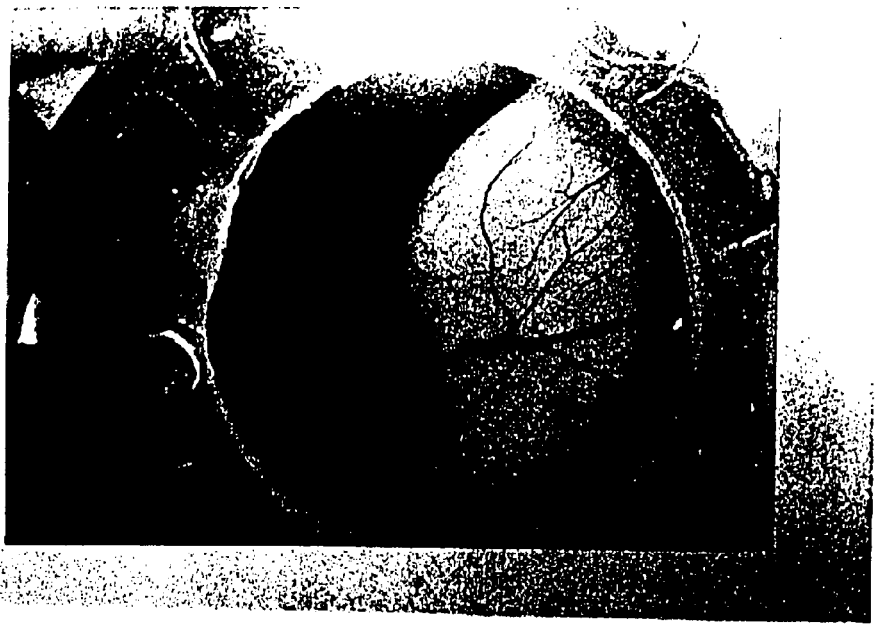
Figure 8B:
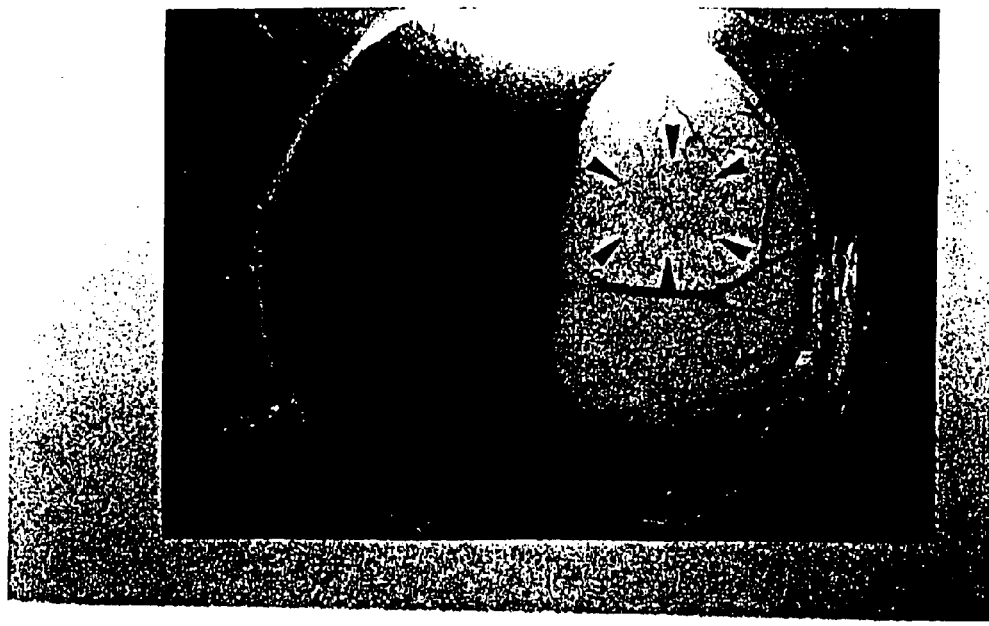
Figure 9A:
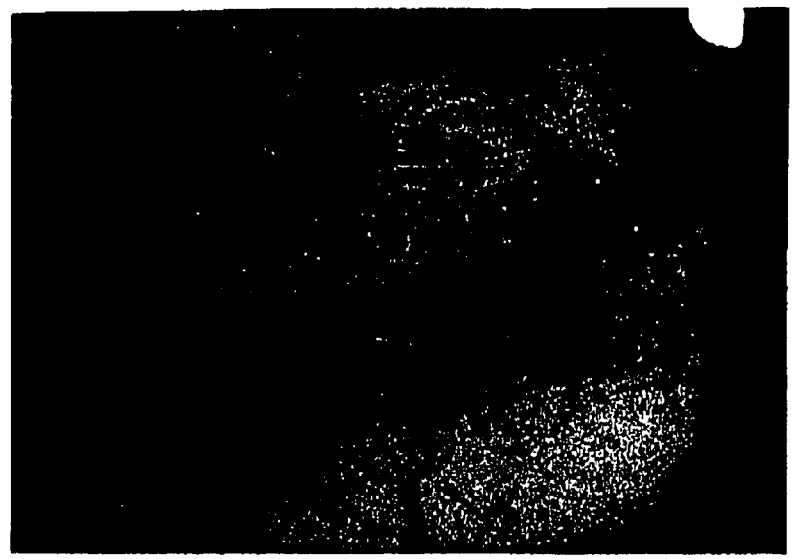
Figure 9B:
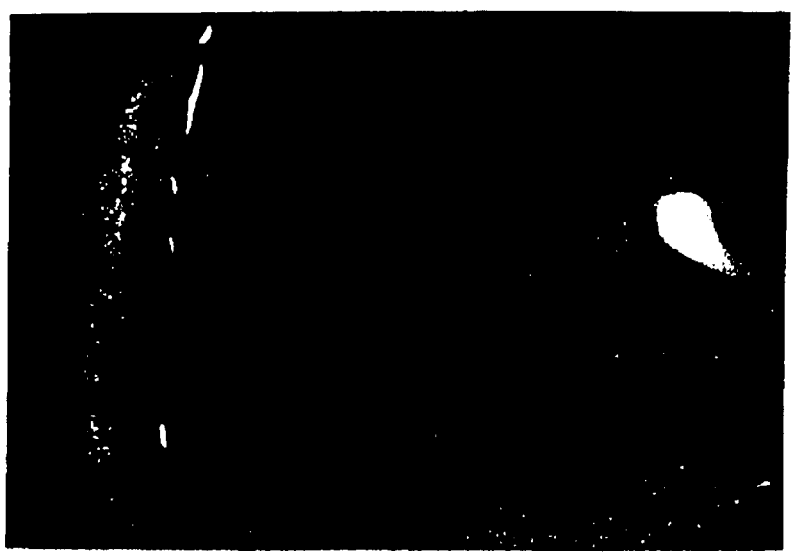
Figure 10A:
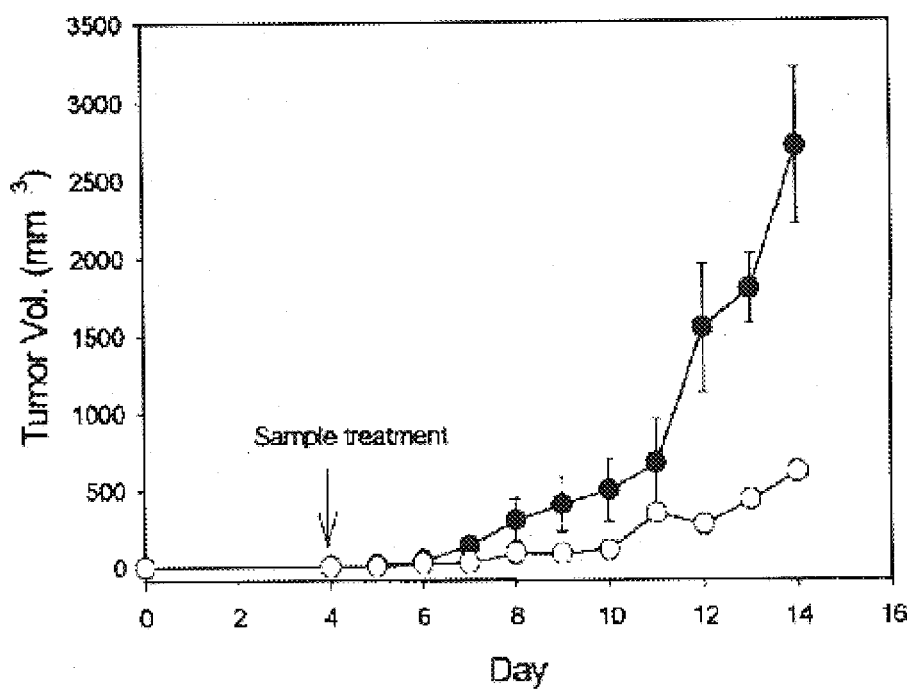
Figure 10B:
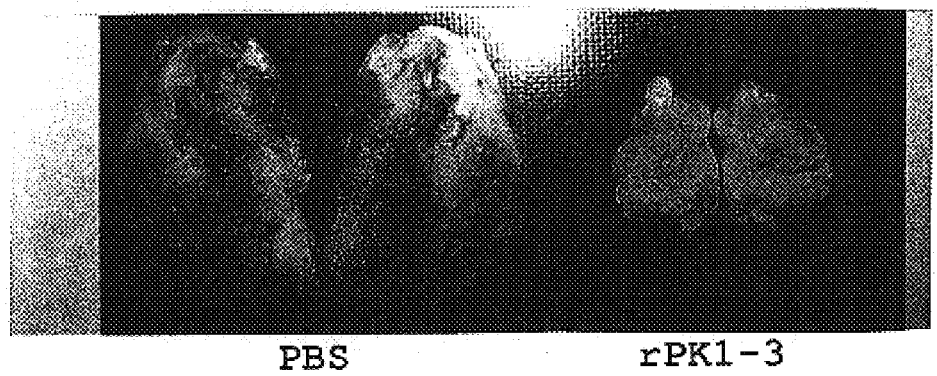
Figure 11:
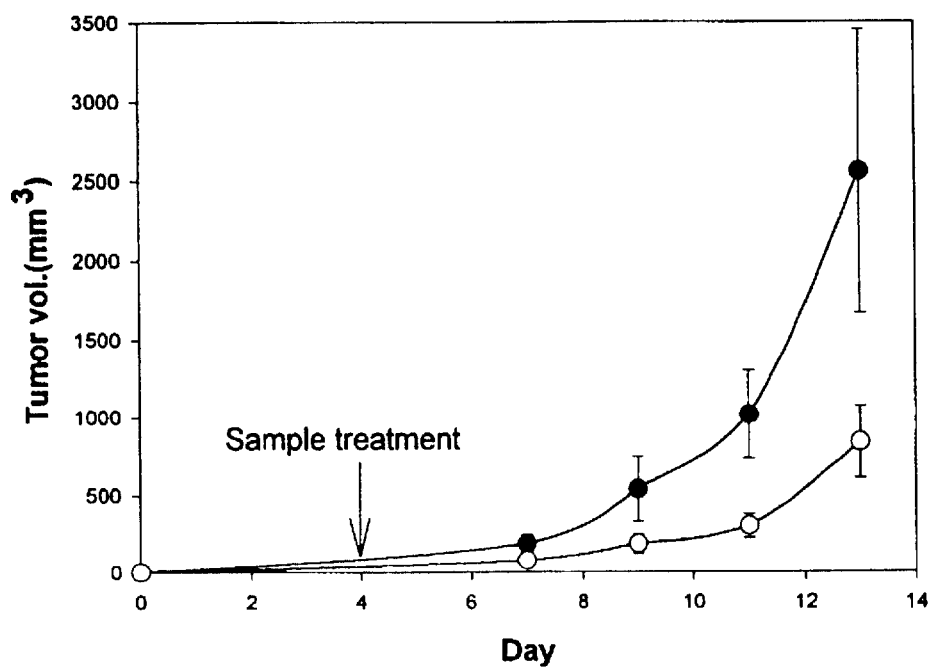

FIG. 8(A–B) represents that greenstatin suppresses angiogenesis in chick embryo chorioallantoic membrane (; CAM), where PBS: PBS-treated egg (control);

rPK1-3: greenstatin-treated egg,

FIG. 9(A–B) represents that greenstatin suppresses the angiogenin-induced angiogenesis in rabbit cornea, where +A: cornea treated with only angiogenin (control);

+A+rPK1-3: cornea treated with both angiogenin and greenstatin,

FIG. 10a represents that greenstatin suppresses the growth of Lewis lung carcinoma in C57BL/6 mouse, where closed circle: tumor volumes in PBS-injected mice; open circle: tumor volumes in greenstatin-injected mice, FIG 10b shows the grown Lewis lung carcinoma of FIG. 10a, where PBS: tumor excised from PBS-injected mouse;

RPK1-3: tumor from greenstatin-injected mouse,

FIG. 11 represents that greenstatin suppresses the growth of skin cancer cells (B16 melanoma), where closed circle: tumor volumes in PBS-injected mice;

open circle: tumor volumes in greenstatin-injected mice, and

Figure 12:
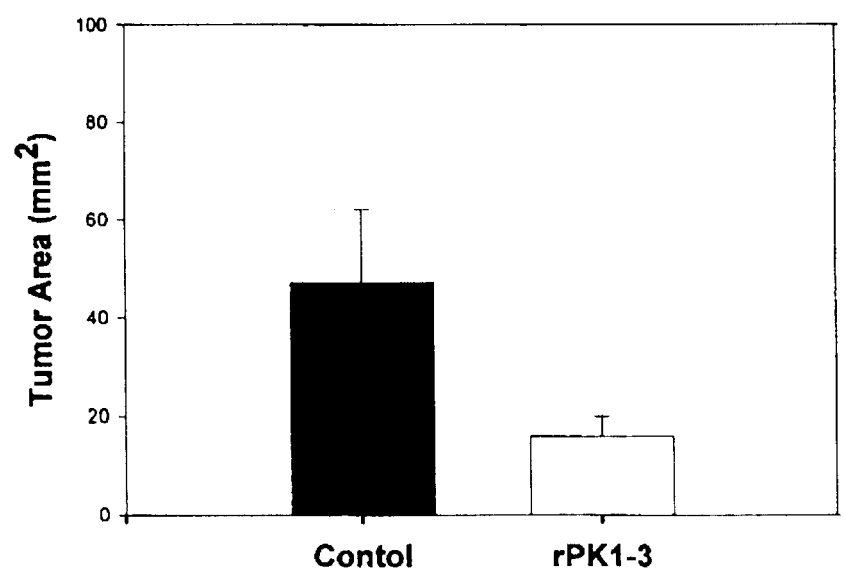

FIG. 12 represents that greenstatin suppresses the growth of human brain tumor (U87 glioma) in nude mouse.

DETAILED DESCRIPTION OF PREFERRED EMBODIMENTS

Hereinafter, the present invention is described in detail.

The present invention provides a process of purifying angiogenesis inhibitor proteins.

To produce the protein in the form of inclusion bodies in *E. coli*, an *E. coli* expression vector is constructed, which contains DNA sequence encoding the angiogenesis inhibitor protein. Also provided is *E. coli* transformant into which the expression vector is introduced.

In such aspect of this invention, the angiogenesis inhibitor proteins include angiostatin™, greenstatin, a protein with kringle structure, a portion of these proteins, and the variants of these proteins. Thus, DNA sequences encoding all these proteins may be used for the construction of the expression vectors and for the production of recombinant angiogenesis inhibitor proteins.

In preferred embodiments, DNA sequence encoding plasminogen kringle 1 to 3 fragment (hereinafter, referred to as "PK1-3") was amplified by PCR using the human fetal liver cDNA library as a template, and METK1/N-NdeI (described by SEQ ID NO: 4) and METK1/C-BamHI (described by SEQ ID NO: 5) as 5' and 3' synthetic oligonuclotide primers, respectively. The METK1/N-NdeI primer recognizes the 350-bp region of plasminogen cDNA and contains NdeI restriction site at its 5' end, while the METK1/C-BamHI primer corresponds 1111-bp region and has BamHI restriction site at its 5' end and a stop codon. The PCR amplifies 804-bp DNA fragments, a full-length PK1-3 DNA sequence with NdeI and BamHI sites at its 5' and 3' ends, respectively.

Figure 1:
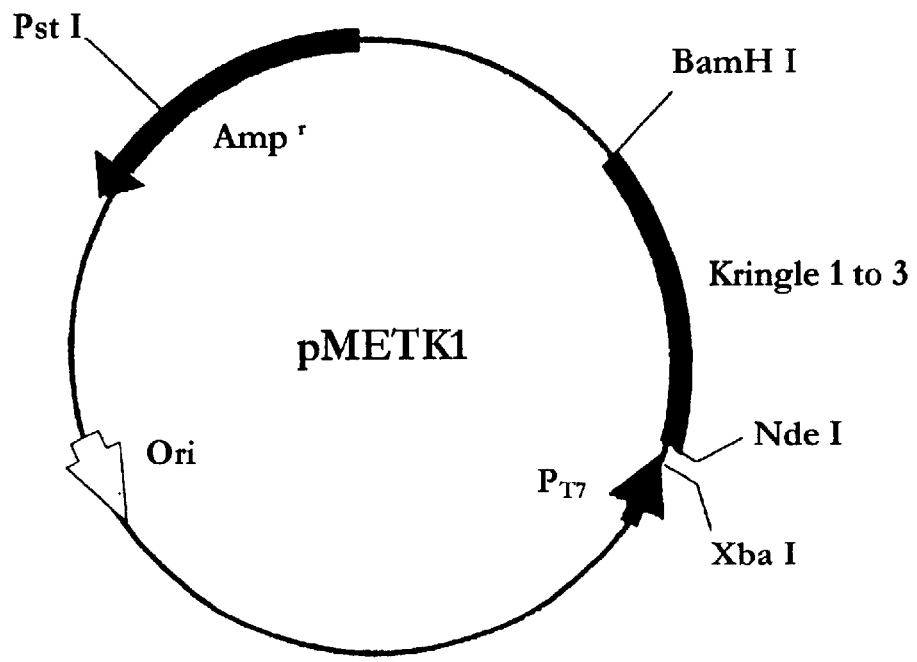
FIG. 1 represents an *E. coli* expression vector pMETK1, which contains greenstatin.

The isolated PK1-3 sequence may be inserted into an appropriate *E. coli* expression vector. In preferred embodiments, the amplified DNA sequence is digested with NdeI and BamHI enzymes, and then the digested DNA is inserted into NdeI/BamHI restriction site of pET11a. The resulting vector was designated pMETK1 (see FIG. 1).

To obtain *E. coli* transformant expressing the angiogenesis inhibitor proteins, the *E. coli* expression vector of this invention may be introduced into an appropriate *E. coli* strain. In a further embodiment, *E. coli* BL21 (DE3) strain is transformed with the expression vector pMETK1. This transformant was designated *E. coli* BL21/ MA001, and deposited in Korean Collection for Type Cultures (KCTC) on May 14, 1998 (Accession NO: KCTC 0476BP).

In the purifying process of this invention, the *E. coli* transformant may be cultured in appropriate medium and harvested to obtain cell lysate, and then the angiogenesis inhibitor protein in the inclusion bodies of the cell lysate may be solubilized and refolded. According to these procedures, the angiogenesis inhibitor proteins can be obtained in active form.

Particularly, the angiogenesis inhibitor protein is isolated from the inclusion bodies of the *E. coli* transformant, and the active form of the protein is obtained through solubilizing and refolding steps that are optimized to the properties of the proteins.

The solubilization is performed using an appropriate chemical condition, in which guanidyl HCl or urea is preferably employed. In a preferred embodiment, 6~8 M guanidyl HCl or urea was employed.

In this invention, refolding step follows the solubilizing step. The refolding step exploits the properties of the angiogenesis inhibitor proteins, whose active forms bind to lysine. Thus, the partial refolding reaction of this invention is performed in a buffer containing basic amino acid, urea, and glutathione. The glutathione in the buffer enhances the formation of disulfide bonds in the proteins. In a preferred embodiment, the basic amino acid is lysine or arginine, and the concentration of urea in the buffer is maintained in the approximate range of 0.1~4 M.

Figure 2:
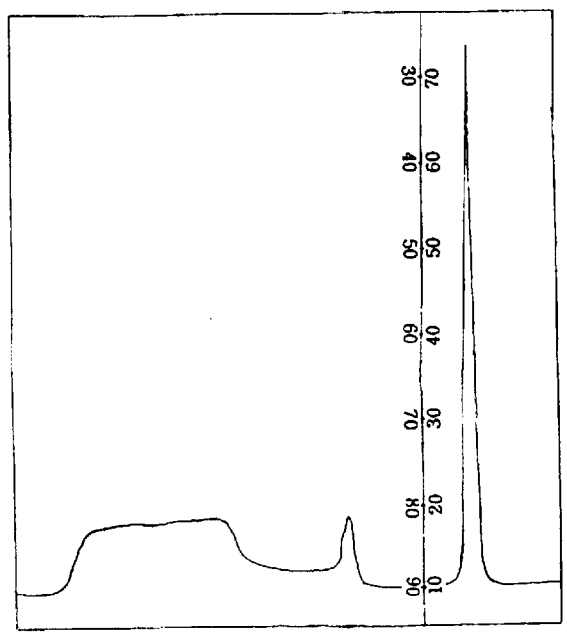
FIG. 2 represents the result of lysine-sepharose chromatography with which refolded greenstatin is purified.

In the present invention, an additional step of dialysis in a buffer may follow the solubilizing and the refolding steps so as to wash out the basic amino acid and other remaining compounds. In a preferred embodiment, a lysine affinity column chromatography is employed for the purification of the refolded proteins (see FIG. 2). In another preferred embodiment, Sp-sepharose ion exchange column chromatography is employed (see FIG. 3). The former exploits the lysine-binding nature of the angiogenesis inhibitor proteins, while the latter exploits their negative-charged nature.

Figure 4:
FIG. 4 represents the non-reducing SDS-polyacrylamide gel electrophoresis of the protein fractions reserved in each step of purification, where Lane 1: *E. coli* cell lysate.

Both dialysis and Sp-sepharose ion exchange column chromatography may be used to wash out the basic amino acid and other remaining compounds (see FIG. 4). While dialysis procedure is more time-consuming and inconvenient than the chromatography, it shows higher purification efficiency (see Table 1).

In another embodiment, the properties of purified greenstatin are identified through N-terminal amino acid sequencing and the analysis of protein secondary structure where circular dichroism is exploited (see FIG. 5). The results of these analyses imply that the purified greenstatin is the same as native greenstatin in secondary structure as well as N-terminal sequence.

According to preferred embodiments, greenstatin specifically suppresses the proliferation of vascular endothelial cells. That is, the purified greenstatin suppresses the angiogenic agent (for example, bFGF)-induced proliferation of bovine capillary endothelial cells (see FIG. 6), while it does not suppress the proliferation of non-endothelial cancer or normal cells (see FIG. 7). Furthermore, it is confirmed that the greenstatin shows higher suppressive efficacy in endothelial growth suppression than native angiostatin™ does (see FIG. 6).

According to another preferred embodiment, the greenstatin inhibits angiogenesis in the development of fertilized egg (see FIG. 8). This suppressive effect is estimated through the analysis using chick embryo chorioallantoic membrane (CAM).

According to still another embodiment, the suppressive effect of the greenstatin on angiogenesis is also confirmed in cornea. Particularly, treatment with the greenstatin leads to the suppression of the angiogenin-induced angiogenesis in rabbit cornea (see FIG. 9). Thus, it is verified that the pharmaceutical composition containing greenstatin is applicable to the treatment of angiogenesis-dependent ophthalmic diseases such as diabetic retinopathy.

According to a preferred embodiment, it is confirmed that the greenstatin can be used as an effective component of anticancer drug. To investigate the anticancer activity, various cancer cells such as lung (see FIGS. 10a and 10b), skin (see FIG. 11), and brain tumor (see FIG. 12) are injected into animals. Treatment with greenstatin to the animals results in the inhibition of tumor growth. Thus, the pharmaceutical composition containing greenstatin is applicable to the treatment of various cancers including the above cancers.

The purified greenstatin of this invention may be formulated with a pharmaceutical vehicle or diluent for oral, intravenous, subcutaneous, intranasal, intrabronchial or rectal administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The greenstatin of this invention may also be employed with sodium lauryl sulfate or other pharmaceutically acceptable detergents to enhance oral bioavailability of such compounds.

The greenstatin of this invention may be administered in a dosage range of about 10~100 mg/kg, preferably 40~80 mg/kg, and may be administered 1~3 times a day.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Cloning of the Gene Encoding Plasminogen Kringle 1–3 (PK1-3)

To amplify DNA sequence encoding the kringle 1 to 3 region of plasminogen, two primers (METK1/N-NdeI and METK1/C-BamHI) were synthesized. The METK1/N-NdeI primer (described by SEQ ID NO: 4) contains NdeI restriction site at its 5' end, recognizing the 350-bp region of plasminogen cDNA. The METK1/C-BamHI primer (described by SEQ ID NO: 5) has BamHI restriction site at the 5' end and a stop codon, corresponding the 1111-bp region.

804-bp DNA fragments containing a full PK1-3 gene were amplified by PCR (; polymerase chain reaction). In the PCR, the METK1/N-NdeI and METK1/C-BamHI oligonucleotides were used as PCR primers and human fetal liver cDNA library (Choi et al., *Mammalian Genome*, 6, 653–657, 1995) as a template. The amplifying cycle was repeated 35 times, comprising denaturation at 94° C. for 1 min, annealing at 50° C. for 1 min, and polymerization at 72° C. for 1.5 min.

The PCR products were digested with NdeI and BamHI restriction enzymes, and then inserted into the NdeI/BamHI site of pET11a (Novagen, USA). The resulting expression vector pMETK1, was introduced into *E. coli* BL21(DE3) strain.

This transformant was designated *E. coli* BL21/MA001, and deposited in Korean Collection for Type Cultures (KCTC) on May 14, 1998 (KCTC Accession NO. 0476BP)

The greenstatin isolated from this transformant has three amino acid residues (Ser-Gly-Cys) at its C-terminal in addition to the polypeptide described by SEQ ID NO: 3.

The procedure for constructing vector pMETK1 was employed for vector pMETK2, in which the DNA sequence encoding three additional residues was deleted. The vector pMETK2 was introduced into *E. coli* BL21(DE3) strain. This transformant was designated *E. coli* BL21-MA002, and deposited in Korean Culture Center of Microorganisms (KCCM) on May 13, 19 (Accession NO: KCCM-10158).

Example 2

The Solubilization of Inclusion Bodies and the Refolding of Greenstatin

Batch culture was employed to obtain media containing the *E. coli* BL21-MA002 strain of Example 1. The media were centrifuged to precipitate cells, which then were resuspended in Tris-EDTA buffer. The resuspended cells were disrupted using Gaulin, and the cell lysate was obtained. After lysozyme, DNase I, and $MgCl_2$ were added to the lysate, the lysate was shaken and centrifuged. The pellet was washed with Tris buffer containing EDTA and detergent.

The washed pellets are the inclusion bodies, which contains the high level of greenstatin. The inclusion bodies were solubilized in Tris buffer containing 6~8 M guanidyl HCl or 6~8 M urea, and β-mercaptoethanol. Refolding reaction was performed, where the solubilized inclusion bodies were diluted with Tris buffer containing the basic amino acid, 0.1–4M urea or guanidyl HCl and glutathione. To eliminate salts and other solutes, the refolded greenstatin was then dialyzed in PBS (; phosphate-buffered saline) or loaded into the ion exchange column.

Example 3

Lysine-sepharose Column Chromatography

The solution containing refolded greenstatin was loaded to lysine affinity column. After the column was washed with PBS containing NaCl, the refolded greenstatin was eluted with PBS supplemented by EACA (ε-aminocaproic acid) (see FIG. 2). The eluted fraction was analyzed by SDS-polyacrylamide gel electrophoresis, showing single protein band on the gel (see FIG. 4). In this chromatography procedure, the purified greenstatin shows above 90% purity.

Example 4

The isolation of Pure Greenstatin Using Sp-sepharose Column Chromatography

Figure 3:
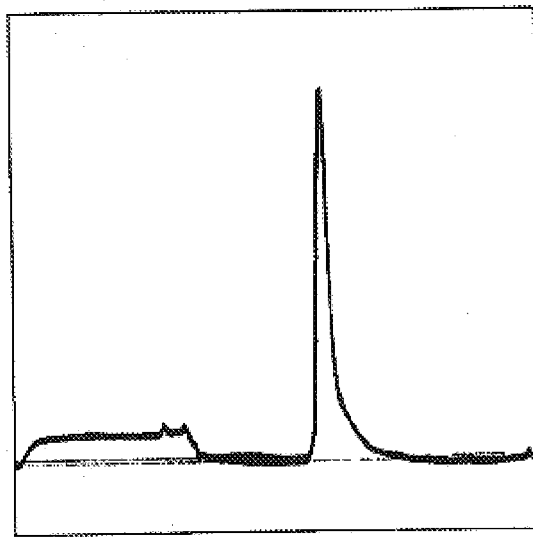
FIG. 3 represents the result of Sp-sepharose chromatography with which the greenstatin fraction of lysine-sepharose column is further purified.

The greenstatin fraction dialyzed in Example 2 was loaded into Sp-sepharose ion exchange column, and then the greenstatin with high purity was eluted with PBS containing NaCl (see FIG. 3, FIG. 4, and Table 1).

TABLE 1

| | Purifying procedures | |
|---|---|---|
| Fraction | Dialysis (mg total protein) | Sp-sepharose column (mg total protein) |
| Inclusion bodies | 4 | 4 |
| Refolding | 3.52 | 3.52 |
| Sp-ion exchange column | 1.33 | 1.50 |
| Lysine affinity column | 1.20 | 0.94 |

Example 5

The Properties of the Purified Greenstatin

N-terminal amino acid sequencing of purified greenstatin was performed with Perkin-Elmer™ protein sequencer 427A, and the secondary structure of the protein was analyzed with JASCO J-715 spectropolarimeter, using the purified greenstatin and native greensatin in 50 mM sodium phosphate buffer (pH 7.4)

The result of N-terminal sequencing revealed that the N-terminal sequence of the purified greenstatin is identical to the sequence following 3rd residue of angiostatin™ sequence, and to the N-terminal sequence described by SEQ ID NO: 3.

Through the analysis of protein secondary structure, it is disclosed that the purified greenstatin has kringle structures (see FIG. 5). The secondary structure of purified greenstatin is identical to that of native greenstatin, which implied that the purified greenstatin has kringle structures as native greenstatin does.

Example 6

The Suppressive Effect of the Purified Greenstatin on the Endothelial Cell Growth Bovine adrenal cortex endothelial cells (; BCE) were cultured in DMEM medium supplemented with 3 ng/ml bFGF, 10% bovine calf serum, and 1% antibiotics, under the condition of 37° C., 5% $CO_2$. Gelatinized 24-well culture plate containing 25,000 cells per well was incubated in DMEM medium supplemented by 5% bovine calf serum and 1% antibiotics, and the plate was then washed with PBS. The same medium or various doses of native angiostatin™ (Calbiochem, USA) or purified greenstatin were added to BSC with the volume of 0.25 ml/well. After incubated at 37° C. for 30 min, the cells were treated with 0.25 ml of medium supplemented by 1 ng/ml bFGF and further incubated for 72 hours. To measure the growth-suppression activities of native angiostatin™ and purified greenstatin, the cells were treated with PBS containing 0.05% trysin and 0.53 mM EDTA, and the removed cells was counted by hemocytometer.

The greenstatin used in this Example and following Examples was purified according to the method of this invention, specifically to the method using a pMETK1 transformant. In addition, the native angiostatin™ in this Example was the recombinant kringle 1–4 peptide which was manufactured using baculovirus system.

According to FIG. 6, while native angiostatin™ showed $ED_{50}$ of 4 μg/ml, greenstatin had $ED_{50}$ of 2 μg/ml, thus approximately 2-fold higher suppressive activity than that of native angiostatin™.

Example 7

The Endothelial-specific Growth Suppression of Greenstatin

According to the almost same procedures of Example 6, it was disclosed that greenstatin specifically suppresses the bFGF (angiogenic agent)-induced growth of endothelial cells. Particularly, we performed the same experiments as Example 6, except that the vascular endothelial cells in Example 6 were replaced by non-endothelial cells such as Lewis lung carcinoma, NTH3T3 cells, and mouse skin fibroblasts.

The result was that greenstatin had no significant effect on the proliferation of the cancer cells or normal cells (see FIG. 7), suggesting that greenstatin has a specific inhibitory effect on endothelial proliferation.

Example 8

The Suppressive Effect of the Purified Greenstatin on Angiogenesis in Fertilized Eggs Fertilized 3-day-old chick eggs (here, regarded as zero-day embryo), bought locally, were incubated at 37° C. under 90% humidity. After 2 days of incubation, 3~4 ml or albumin was eliminated by a syringe. After further incubation for 3 days, a window was made on the eggs so that either greenstatin or PBS was applied to the CAM (chorioallantoic membrane) of the 5-day embryo through the window. Intaglios (Korea Green Cross Corp.) was injected into the CAM of 7-day embryo, and the inhibition of angiogenesis was measured by observing the CAM.

According to FIG. 9, greenstatin-treated embryo showed the inhibition of capillary formation when compared with PBS control.

Example 9

The Suppressive Effect of Greenstatin on Angiogenesis in Rabbit Eyes

Male rabbits (2 to 2.5 kg) were used. With a cataract knife, an intrastromal linear keratotomy was performed and a lamellar micropocket was dissected with a 1-mm wide pliable iris spatula at 1.2-mm apart from the superior limbus. Two disks containing 500 ng angiogenin and containing 20 μg greenstatin, respectively, were inserted in line into the micropocket, positioned 1.2-mm away from the superior corneal limbus of 13 rabbits. The control group underwent the same treatment, except for the insertion of PBS instead of greenstatin. The observation of vascular tissues was performed by means of slit-lamp microscopy and photography.

When compared with angiogenin-applied control group, test group which was treated with both angiogenin and purified greenstatin, showed the suppression of angiogenin-induced angiogenesis (see FIG. 9). Thus, it was verified that the greenstatin of this invention suppresses the angiogenin-induced angiogenesis in rabbit eyes.

Example 10

The Suppressive Effect of Greenstatin on the Growth of Lung and Skin Cancer in C57BL/6 Mice To estimate the tumor suppression activity of an angiogenesis inhibitor greenstatin, mouse lung cancer cells (Lewis lung carcinoma) and mouse skin cancer cells (B16 melanoma) were employed. The cancer cells were uniformly diluted with PBS to the concentration of $1 \times 10^6$ cells/ml, and 0.2 ml of the cell suspensions was subcutaneouly injected into the dorsal part of 8-week-old C57BL/6 mice. On 6th day after the injection, greenstatin (100 mg/kg/day) or PBS was subcutaneouly injected everyday for 10 days. Test and control groups consisted of 5 mice. The size of tumor was measured by caliper and the volume of tumor was estimated according to the calculation, Volume=(Area)$^2$×Height×0.52.

As result, the growth of mouse lung and skin tumor was suppressed by greenstatin (see FIGS. 10a, 10b, and 11).

Example 11

The Suppressive Effect of Greenstatin on the Brain Tumor Growth in Nude Mouse

To inquire whether the greenstatin can suppress the growth of human tumors, brain tumor (U87 glioma) was employed. 2 ml of the tumor cell suspension ($1 \times 10^6$ cells/ml in PBS) was injected into the brain of 6 to 8-week-old nude mice. After 7 days when tumor grew in brain, greenstatin (100 mg/kg/day) was subcutaneously injected into the dorsal part of test mice, while PBS was injected into control mice. The test and control groups consisted of 5 mice, respectively. At 15 to 20 days after the daily administration of greenstatin, the mice were sacrificed and autopsied, and the brains were excised to measure the area of tumor section.

The result indicated that the brain tumor growth was suppressed by greenstatin (see FIG. 12).

Example 11 Acute Toxicity Test Using Rat

We carried out following experiment to find out the acute toxicity of greenstatin.

Acute toxicity was examined using 6-week-old SPF SD type rat. 1 ml of PBS containing greenstatin (dose: 1 g/kg) was subcutaneouly injected into two rats per experimental group. After injection, the rats were observed in terms of clinic symptom and change in weights of rats, and brought to blood test and autopsy so as to investigate the abnormalities of abdominal and thoracic organs. As a result, all tested animals were survived, and there was no striking clinic symptom, change in weights or other toxic effect. The examined compound did not elicit any toxic effect when injected to rats within the range of 1 g/kg, thus proved to be safe compound for parenteral administration.

INDUSTRIAL APPLICABILITY

Although angiogenesis inhibitor proteins can be produced in *E. coli* expression system inexpensively and conveniently, it is hard to refold the recombinant proteins of the inclusion bodies. According to the present invention, the active forms of the inhibitor proteins are inexpensively purified, since solubilizing and refolding reactions of the purifying process exploit the properties of the proteins. Greenstatin, purified according to the purifying process, is specifically suppress the proliferation of vascular endothelial cells, and also applicable to the treatment of angiogenesis-dependent diseases such as various cancers, glaucoma, retinopathy, arthritis, and psoriasis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A process of purifying a greenstatin protein consisting of SEQ ID NO: 3, comprising the steps of;
   1) solubilizing the greenstatin protein produced in the form of inclusion bodies in *E. coli* with a buffer containing urea or guanidyl HCl; and
   2) refolding the solubilized fraction of step 1) in a buffer containing 0.1~4 M urea, glutathione, and at least one basic amino acid selected from the group consisting of lysine and arginine.

2. The process of claim 1, which fisher comprises an additional step, wherein the basic amino acid is washed out from the buffer, using an ion exchange column chromatography.

3. The process of claim 1, which further comprises an additional step, wherein a protein fraction is dialyzed in a buffer selected from the group consisting of phosphate-buffered saline and Tris buffer.

4. The process of claim 1, which further comprises an additional step, wherein at least one kind of chromatography is performed, selected from the group consisting of lysine affinity column chromatography and Sp-sepharose ion exchange column chromatography.

5. The process of claim 1, wherein the greenstatin protein of step 1) is obtained by constructing *E. coli* expression vector containing DNA encoding the greenstatin protein, transforming an *E. coli* with the *E. coli* expression vector to obtain an *E. coli* transformant, and culturing the *E. coli* transformant to express the greenstatin protein.

6. The process of claim 5, wherein the *E. coli* transformant is *Escherichia coli* BL21/ MA002 deposited as KCCM-10158.

7. A process of producing a greenstatin protein consisting of SEQ ID NO: 3, comprising the steps of;

1) constructing an *E. coli* expression vector containing DNA encoding the greenstatin protein consisting of SEQ ID NO: 3, 2) transforming *E. coli* with the vector of step 1); and 3) solubilizing and refolding the protein produced in the form of inclusion bodies in the *E. coli* transformant.

8. An *E. coli* transformant BL21MA002 (accession NO: KCCM-10158), produced by the transformation of *E. coli* BL21 (DE3) strain with pMETK2.

\* \* \* \* \*

SEQUENCE LISTING

<160> NUMBER OF SEQ ID NOS: 5

<210> SEQ ID NO 1
<211> LENGTH: 810
<212> TYPE: PRT
<213> ORGANISM: Homo Sapiens

<400> SEQUENCE: 1

Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu

-continued

```
            35                  40                  45
Cys Ala Ala Lys Cys Glu Glu Asp Glu Glu Phe Thr Cys Arg Ala Phe
             50                  55                  60
Gln Tyr His Ser Lys Glu Gln Gln Cys Val Ile Met Ala Glu Asn Arg
 65                  70                  75                  80
Lys Ser Ser Ile Ile Ile Arg Met Arg Asp Val Val Leu Phe Glu Lys
                 85                  90                  95
Lys Val Tyr Leu Ser Glu Cys Lys Thr Gly Asn Gly Lys Asn Tyr Arg
                100                 105                 110
Gly Thr Met Ser Lys Thr Lys Asn Gly Ile Thr Cys Gln Lys Trp Ser
            115                 120                 125
Ser Thr Ser Pro His Arg Pro Arg Phe Ser Pro Ala Thr His Pro Ser
        130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Cys Met His Cys Ser Gly Glu Asn
            180                 185                 190
Tyr Asp Gly Lys Ile Ser Lys Thr Met Ser Gly Leu Glu Cys Gln Ala
            195                 200                 205
Trp Asp Ser Gln Ser Pro His Ala His Gly Tyr Ile Pro Ser Lys Phe
        210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
            260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
        290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
            340                 345                 350
Asp Ser Ser Pro Val Ser Thr Glu Gln Leu Ala Pro Thr Ala Pro Pro
            355                 360                 365
Glu Leu Thr Pro Val Val Gln Asp Cys Tyr His Gly Asp Gly Gln Ser
        370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
            435                 440                 445
Cys Asn Leu Lys Lys Cys Ser Gly Thr Glu Ala Ser Val Val Ala Pro
        450                 455                 460
```

-continued

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
            485                 490                 495

Val Thr Gly Thr Pro Cys Gln Asp Trp Ala Ala Gln Glu Pro His Arg
        500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 2
<211> LENGTH: 369
<212> TYPE: PRT
<213> ORGANISM: Homo Sapiens

<400> SEQUENCE: 2

Tyr Leu Ser Glu Cys Lys Thr Gly Asn Gly Lys Asn Tyr Arg Gly Thr
1               5                   10                  15

Met Ser Lys Thr Lys Asn Gly Ile Thr Cys Gln Lys Trp Ser Ser Thr

|   |   |   | 20 |   |   |   | 25 |   |   |   | 30 |   |
|---|---|---|---|---|---|---|---|---|---|---|---|---|

```
Ser Pro His Arg Pro Arg Phe Ser Pro Ala Thr His Pro Ser Glu Gly
        35                  40                  45

Leu Glu Glu Asn Tyr Cys Arg Asn Pro Asp Asn Asp Pro Gln Gly Pro
    50                  55                  60

Trp Cys Tyr Thr Thr Asp Pro Glu Lys Arg Tyr Asp Tyr Cys Asp Ile
65                  70                  75                  80

Leu Glu Cys Glu Glu Cys Met His Cys Ser Gly Glu Asn Tyr Asp
                85                  90                  95

Gly Lys Ile Ser Lys Thr Met Ser Gly Leu Glu Cys Gln Ala Trp Asp
                100                 105                 110

Ser Gln Ser Pro His Ala His Gly Tyr Ile Pro Ser Lys Phe Pro Asn
            115                 120                 125

Lys Asn Leu Lys Lys Asn Tyr Cys Arg Asn Pro Asp Arg Glu Leu Arg
        130                 135                 140

Pro Trp Cys Phe Thr Thr Asp Pro Asn Lys Arg Trp Glu Leu Cys Asp
145                 150                 155                 160

Ile Pro Arg Cys Thr Thr Pro Pro Ser Ser Gly Pro Thr Tyr Gln
                165                 170                 175

Cys Leu Lys Gly Thr Gly Glu Asn Tyr Arg Gly Asn Val Ala Val Thr
                180                 185                 190

Val Ser Gly His Thr Cys Gln His Trp Ser Ala Gln Thr Pro His Thr
            195                 200                 205

His Asn Arg Thr Pro Glu Asn Phe Pro Cys Lys Asn Leu Asp Glu Asn
        210                 215                 220

Tyr Cys Arg Asn Pro Asp Gly Lys Arg Ala Pro Trp Cys His Thr Thr
225                 230                 235                 240

Asn Ser Gln Val Arg Trp Glu Tyr Cys Lys Ile Pro Ser Cys Asp Ser
                245                 250                 255

Ser Pro Val Ser Thr Glu Gln Leu Ala Pro Thr Ala Pro Pro Glu Leu
            260                 265                 270

Thr Pro Val Val Gln Asp Cys Tyr His Gly Asp Gly Gln Ser Tyr Arg
        275                 280                 285

Gly Thr Ser Ser Thr Thr Thr Thr Gly Lys Lys Cys Gln Ser Trp Ser
    290                 295                 300

Ser Met Thr Pro His Arg His Gln Lys Thr Pro Glu Asn Tyr Pro Asn
305                 310                 315                 320

Ala Gly Leu Thr Met Asn Tyr Cys Arg Asn Pro Asp Ala Asp Lys Gly
                325                 330                 335

Pro Trp Cys Phe Thr Thr Asp Pro Ser Val Arg Trp Glu Tyr Cys Asn
                340                 345                 350

Leu Lys Lys Cys Ser Gly Thr Glu Ala Ser Val Val Ala Pro Pro Pro
        355                 360                 365

Val
```

<210> SEQ ID NO 3
<211> LENGTH: 254
<212> TYPE: PRT
<213> ORGANISM: Homo Sapiens

<400> SEQUENCE: 3

```
Ser Glu Cys Lys Thr Gly Asn Gly Lys Asn Tyr Arg Gly Thr Met Ser
1               5                   10                  15

Lys Thr Lys Asn Gly Ile Thr Cys Gln Lys Trp Ser Ser Thr Ser Pro
```

-continued

```
                         20                  25                  30
       His Arg Pro Arg Phe Ser Pro Ala Thr His Pro Ser Glu Gly Leu Glu
                35                  40                  45

Glu Asn Tyr Cys Arg Asn Pro Asp Asn Asp Pro Gln Gly Pro Trp Cys
                50                  55                  60

Tyr Thr Thr Asp Pro Glu Lys Arg Tyr Asp Tyr Cys Asp Ile Leu Glu
       65                  70                  75                  80

Cys Glu Glu Glu Cys Met His Cys Ser Gly Glu Asn Tyr Asp Gly Lys
                        85                  90                  95

Ile Ser Lys Thr Met Ser Gly Leu Glu Cys Gln Ala Trp Asp Ser Gln
                       100                 105                 110

Ser Pro His Ala His Gly Tyr Ile Pro Ser Lys Phe Pro Asn Lys Asn
                       115                 120                 125

Leu Lys Lys Asn Tyr Cys Arg Asn Pro Asp Arg Glu Leu Arg Pro Trp
               130                 135                 140

Cys Phe Thr Thr Asp Pro Asn Lys Arg Trp Glu Leu Cys Asp Ile Pro
       145                 150                 155                 160

Arg Cys Thr Thr Pro Pro Ser Ser Gly Pro Thr Tyr Gln Cys Leu
                           165                 170                 175

Lys Gly Thr Gly Glu Asn Tyr Arg Gly Asn Val Ala Val Thr Val Ser
                       180                 185                 190

Gly His Thr Cys Gln His Trp Ser Ala Gln Thr Pro His Thr His Asn
                       195                 200                 205

Arg Thr Pro Glu Asn Phe Pro Cys Lys Asn Leu Asp Glu Asn Tyr Cys
                       210                 215                 220

Arg Asn Pro Asp Gly Lys Arg Ala Pro Trp Cys His Thr Thr Asn Ser
       225                 230                 235                 240

Gln Val Arg Trp Glu Tyr Cys Lys Ile Pro Ser Cys Asp Ser
                           245                 250
```

<210> SEQ ID NO 4
<211> LENGTH: 33
<212> TYPE: DNA
<213> ORGANISM: Artificial Sequence
<220> FEATURE:
<223> OTHER INFORMATION: PCR primer METK1/N-NdeI

<400> SEQUENCE: 4
cgggatccca tatgtcagag tgcaagactg gga                          33

<210> SEQ ID NO 5
<211> LENGTH: 37
<212> TYPE: DNA
<213> ORGANISM: Artificial Sequence
<220> FEATURE:
<223> OTHER INFORMATION: PCR primer METK1/C-BamHI

<400> SEQUENCE: 5 cgggatccttt actaggagtc acaggacggt atcttac                     37